(12) United States Patent
Wu et al.

(10) Patent No.: US 8,398,325 B2
(45) Date of Patent: Mar. 19, 2013

(54) ORAL CARE IMPLEMENT WITH LIQUID DELIVERY SYSTEM

(75) Inventors: Donghui Wu, Bridgewater, NJ (US); John P. Rouse, Hillsborough, NJ (US); John Gatzemeyer, Hillsborough, NJ (US); Sharon Kennedy, Randallstown, MD (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 12/994,342

(22) PCT Filed: May 23, 2008

(86) PCT No.: PCT/US2008/064630
§ 371 (c)(1),
(2), (4) Date: Nov. 23, 2010

(87) PCT Pub. No.: WO2009/142643
PCT Pub. Date: Nov. 26, 2009

(65) Prior Publication Data
US 2011/0076090 A1    Mar. 31, 2011

(51) Int. Cl.
*A46B 11/02* (2006.01)
(52) U.S. Cl. .................................... 401/188 R; 401/270
(58) Field of Classification Search .............. 401/188 R, 401/270
See application file for complete search history.

(56) References Cited

U.S. PATENT DOCUMENTS

| | | | |
|---|---|---|---|
| 3,389,468 A | 6/1968 | Lewis et al. | |
| 4,519,751 A * | 5/1985 | Beckman et al. | 417/322 |
| 5,403,105 A | 4/1995 | Jameson | |
| 5,476,333 A | 12/1995 | Matthews | |
| 5,476,384 A | 12/1995 | Giuliani et al. | |
| 5,642,994 A | 7/1997 | Chipian et al. | |
| 5,785,956 A | 7/1998 | Sullivan et al. | |
| 6,164,967 A * | 12/2000 | Sale et al. | 433/80 |
| 6,648,641 B1 * | 11/2003 | Viltro et al. | 433/80 |
| 2001/0002228 A1 | 5/2001 | Owens | |
| 2002/0090252 A1 * | 7/2002 | Hall et al. | 401/286 |

(Continued)

FOREIGN PATENT DOCUMENTS

DE  2526640  12/1976
DE  102004057737  3/2006

(Continued)

OTHER PUBLICATIONS

International Search Report and Written Opinion of the International Searching Authority [EP] for corresponding International Application No. PCT/US2008/064630 mailed Apr. 15, 2009.

(Continued)

*Primary Examiner* — David Walczak
*Assistant Examiner* — Bradley Oliver

(57) ABSTRACT

An oral care implement (1) includes a head (12), a handle (10), a neck portion (11) connecting the head and the handle, and a reservoir (15) which contains at least one active agent. The implement has an activator (22) for activating a delivery device which delivers the active agent to one or more outlets (50). A powered delivery device (18) disposed in the head to deliver a liquid from the reservoir via the outlet. A wide variety of types of active agents may be administered at appropriate and accurate doses for therapeutic, hygienic, and/or other benefit.

15 Claims, 10 Drawing Sheets

U.S. PATENT DOCUMENTS

| | | | |
|---|---|---|---|
| 2005/0238412 A1* | 10/2005 | Jacobs et al. | 401/270 |
| 2007/0154863 A1 | 7/2007 | Cai et al. | |
| 2007/0166663 A1 | 7/2007 | Telles et al. | |
| 2008/0118300 A1 | 5/2008 | Burrowes | |

FOREIGN PATENT DOCUMENTS

| | | |
|---|---|---|
| WO | WO 00/15076 | 3/2000 |
| WO | WO 02/58508 | 8/2002 |
| WO | WO 2006/100627 | 9/2006 |
| WO | WO 2007/008908 | 1/2007 |
| WO | WO 2007/073917 | 7/2007 |

OTHER PUBLICATIONS

International Search Report and Written Opinion of the International Searching Authority [EP] for International Application No. PCT/US2008/066828 mailed Feb. 26, 2009.

* cited by examiner

ORAL CARE IMPLEMENT WITH LIQUID DELIVERY SYSTEM

CROSS-REFERENCE TO RELATED PATENT APPLICATIONS

The present application is a national stage entry under 35 U.S.C. §371 of International Patent Application No. PCT/US2008/064630, filed May 23, 2008, the entirety of which is hereby incorporated by reference.

BACKGROUND OF THE INVENTION

The present invention is directed to an oral care implement including a delivery system for a fluid. Oral care implements, particularly toothbrushes, are typically used by applying toothpaste to a bristle section followed by brushing regions of the oral cavity, e.g., the teeth, tongue, and/or gums. Some toothbrushes have been equipped with fluid reservoirs and systems for delivering auxiliary active agents, such as whitening agents, breath freshening agents, and the like.

Some efforts have been made to configure toothbrushes to deliver active agents at the time of brushing. Commonly assigned U.S. 2007/0154863 A1, for example, describes an oral care implement having a reservoir containing an active agent and a user-activated pump for delivering the active agent through a channel and out of one or more outlets.

BRIEF SUMMARY OF THE INVENTION

The present invention is directed to an oral care implement including a delivery system for a fluid.

In one aspect, the oral care implement may have a displaceable reservoir, which contains a liquid substance.

In one aspect, the oral care implement may have a delivery device actuator, such as a switch, for activating a delivery device, such as a pump disposed in the head or other portion of the implement. The delivery device may deliver a predetermined amount of the substance, to one or more outlets. The outlets may be located in the vicinity of the tooth cleaning elements, e.g., bristles, and/or other portion(s) of the oral care implement.

The oral care implement enables a wide variety of active agents to be administered for therapeutic, hygienic, and/or other benefits, such as fresh breath, tooth whitening, reducing sensitivity of the teeth or producing sensations of heat, cool, or tingling.

The oral care implement advantageously may be manufactured at relatively low cost, is easy to use, and may deliver a medium through one or more outlets upon a user activating a switch. By locating a reservoir in the neck portion, the distance that the medium is dispensed to the head is minimized. With this configuration, the implement also is less prone to clogging, the volume of the reservoir may be reduced, and the reservoir may be more easily replaced for changing or replenishment of the active agent.

DETAILED DESCRIPTION OF THE INVENTION

Figure 1:
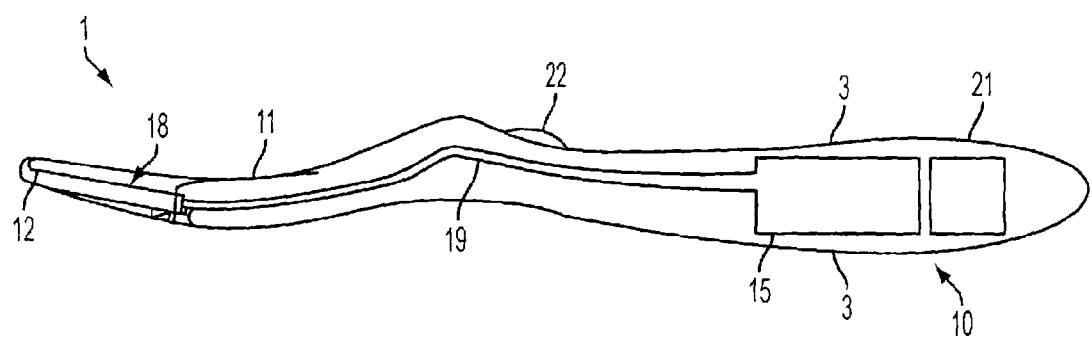
FIG. 1 is a side elevation view of a toothbrush construction having a liquid delivery system.

FIG. 1 schematically illustrates a toothbrush 1 having a handle 10, a head 12, and a neck portion 11 connecting the handle 10 and head 12. The head contains tooth cleaning elements 5, such as bristles and/or elastomeric cleaning elements or the like. A reservoir 15 is provided in the handle 10 for storing a liquid medium having an active agent. In an alternative construction shown in FIGS. 7-11, the reservoir 15 may be provided within the neck portion 11 of the toothbrush. The handle 10 or other exterior portion of the toothbrush 1 may contain a delivery device actuator or switch, such as a user-actuated button 22, for activating a delivery device, such as a pump 18. The pump 18 may be located upstream or downstream of the reservoir 15.

Figure 2:
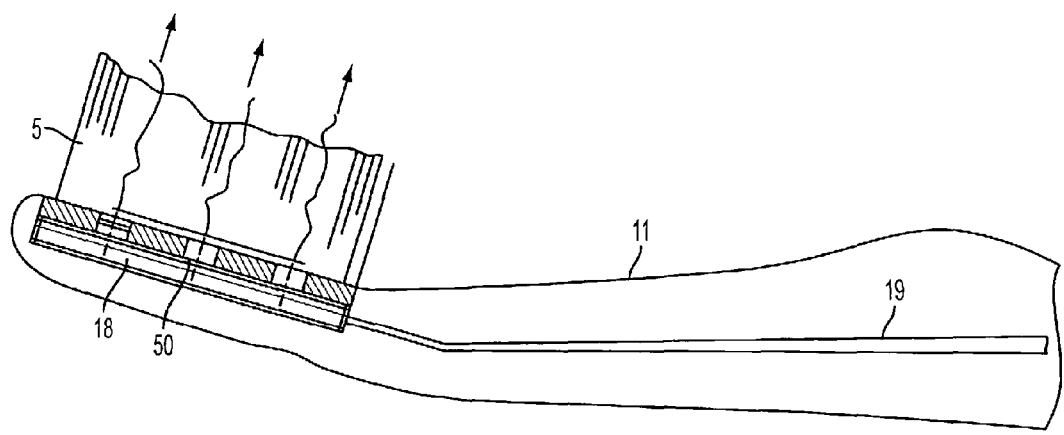
FIG. 2 illustrates an enlarged fragmentary cross-section view of the toothbrush construction of FIG. 1 including a powered delivery device in the head of the toothbrush.

In one construction, a micro piezoelectric pump 18 is positioned beneath the cleaning elements 5 in the toothbrush head. In order to deliver active ingredients or active agents to a desirable location or to avoid clogging from residue toothpaste, the outlet(s) of the micro piezoelectric pump 18 are located at desirable locations, such as, in the vicinity of the bristles (top of the brush head), on the side of the brush head opposite the cleaning elements (bottom of the brush head), at the distal tip of the brush head (the very front tip of the brush), or on the sidewalls of the brush head. Upon activation of the switch 22, the pump 18 draws a quantity of the medium from the reservoir 15 through a channel toward the head. The medium is delivered through one or more outlets 50 located within the bristle field. As shown in FIG. 2, outlets 50 may be spaced along the length of the bristle section to help disperse the medium throughout the bristle field. Optionally, a plurality of outlets may be provided on both the surface of the head that contains the tooth cleaning elements as well as the opposite the surface of the head, e.g., for delivering the same active agent from a common supply or different active agents from separate supplies.

In one construction, the bristles comprised hollow lumens or the like and the liquid medium having an active agent is delivered through the bristles. The liquid may also be delivered simultaneously through outlets 50 located at different portions of the toothbrush 1, for example to aid in the application of the active agent to different areas of the mouth. Although reference is made to a plurality of outlets, it is contemplated that a single outlet could be used.

The switch for activating the pump 18 may be a button 22, as illustrated in FIG. 1, or it may be another type of switch such as a touch or heat sensitive type of switch, user-activated toggle switch, rotating dial. Engaging the button 22, such as, by depressing the button 22, may activate a timing circuit which causes the pump 18 to operate for a period of time which, in turn, causes a predetermined amount of the medium containing the active agent to be pumped from the reservoir 15 and through the outlets 50. The pump has a power source, such as a battery 21, which may be located in the handle portion 10. The timing circuit causes the pump 18 to operate for a time period which either may be preset or may be adjustable, for example, by using a slidable variable control, rotatable variable dial or digital preset control. The time interval also may vary depending on the active agent or the amount of time programmed by the user or manufacturer.

The medium containing the active agent may be incorporated into a sealed reservoir 15 during manufacture of the toothbrush 1, in which case the toothbrush 1 may be disposed of after the supply of the active agent is exhausted. Alternatively, the reservoir 15 may be refillable through an inlet (not shown), or may be replaceable, e.g., by inserting a replaceable cartridge into a recess in the toothbrush. A cartridge may be provided with a sharpened element which penetrates a membrane in the recess to permit the medium to flow from the cartridge. The cartridge may be spring-loaded to stay in place after insertion into the recess, and can have a seal to prevent unwanted leakage of the active agent. The cartridge may be disposable or refillable. Other methods of providing a refillable and/or replaceable cartridge or the like may be used.

The pump 18 may be coupled to the head 12 by various known methods including bonding, molding, melting, and mechanical fixing. The pump 18 can also be integrated into the head 12 to save space and cost by bonding/molding drive element directly in a cavity in the head. Alternatively, the pump 18 or the reservoir 15 may be coupled to the handle portion 10 of the toothbrush 1 by similar means.

Referring to FIG. 1, reservoir 15 can be provided in a displaceable construction, such as a collapsible bag or container, connected to the micro piezoelectric pump 18 via a fluid pathway 19, such as flexible tubing. The tubing can be embedded in the brush handle 10 or a channel directly molded in the brush handle. The reservoir 15, when provided as a collapsible bag or container, may be used so that air bubbles are not generated during transportation of active ingredients or agents and brushing. In addition, the collapsible bag or container ensures that negative pressure does not build up in the container as to reduce pumping rate after a portion of active ingredients or agents has been withdrawn by the micro piezoelectric pump 18. The collapsible bag or container can store enough material for about 60-120 uses, where each use will consume about 10-50 µL (micro-liters) of fluid or 10-100 µL of fluid. Nevertheless, other values are possible.

Figure 3A:
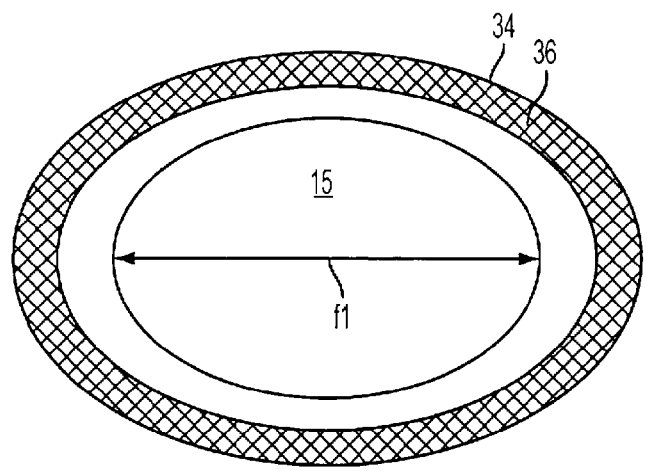
FIGS. 3A-3C are schematic cross-section views taken along line 3-3 in FIG. 1 showing a displacement of a reservoir as a liquid is withdrawn from the reservoir.
Figure 3B:
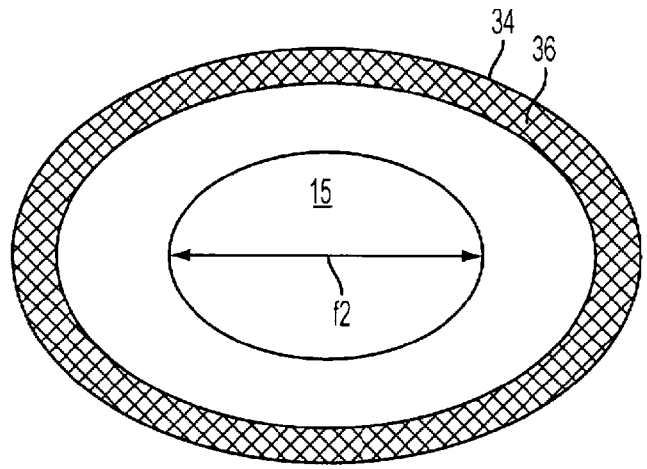
Figure 3C:
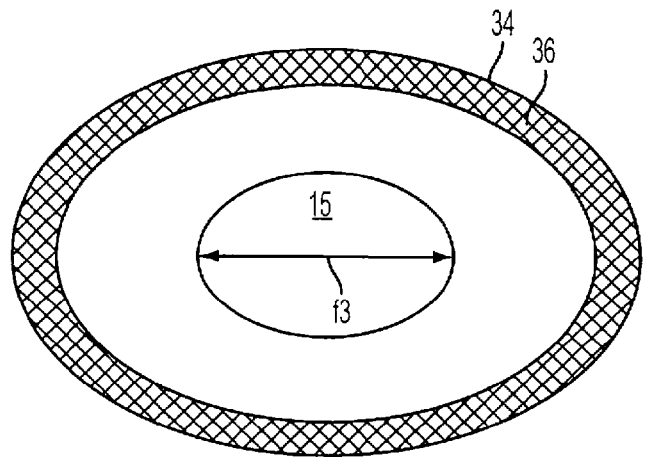

FIGS. 3A-3C show cross-sectional views of the toothbrush 1, taken along line 3-3 in FIG. 1. FIGS. 3A-3C show the radial displacement of the compressible reservoir 15 as liquid is depleted from the reservoir, with f1, f2, and f3 representing the width of the reservoir in FIGS. 3A, 3B, and 3C, respectively. The width as used here is one of the many ways that may be used to measure the radial displacement. The elements 34 and 36 represent the surface and thickness of the toothbrush body, respectively. As can be appreciated, as the pump 18 operates, negative pressure (e.g. suction pressure) is provided in the tubing and reservoir. As the liquid in the reservoir 15 is depleted by flowing to the head 12, the reservoir 15 is compressed to maintain fluid contact with the pump. For example, FIG. 3A shows a reservoir with a width of f1 when the liquid is at a maximum. As the liquid is depleted by flowing to the toothbrush head portion 12 via the flexible tube 19 and pump 18, the width of reservoir 15 becomes smaller as shown in FIG. 3B, where f2 is less than f1. As the liquid is further depleted the reservoir 15 is compressed further as shown in FIG. 3C, having width f3, where f3 is less than f2. Hence, width f3 is less than width f2 and width f1 is less that width f2. Nevertheless, the container may become smaller in the longitudinal axial direction during operation of the pump 18. With respect to longitudinal displacement, the distal end of the reservoir may displace in the direction of the head of the toothbrush.

The active agent may be delivered in a dose appropriate for its intended purpose. The amount may be controlled by controlling the duration the pump 18 operates after the button 22 is pressed. The duration of dispensation will depend on the desired dose and the flow rate of the medium, and typically ranges from about 1 second to 5 minutes, often from about 5 seconds to about 2 minutes, and may range from about 10 seconds to 30 seconds. The dispensing action may begin either immediately after the button 22 is pressed, or a predetermined delay may be programmed.

Suitable devices are commercially available for delivering the medium from the reservoir 15 to the outlet(s). The pump may deliver the medium through a variety of different actions that are mechanical, electrical, or a combination thereof, depending on the pump structure. In one example, a micro piezoelectric pump, such as model mp5, manufactured by Bartels Mikrotechnik GmbH may be used. Nevertheless, other pumping devices can be used.

Figure 4:
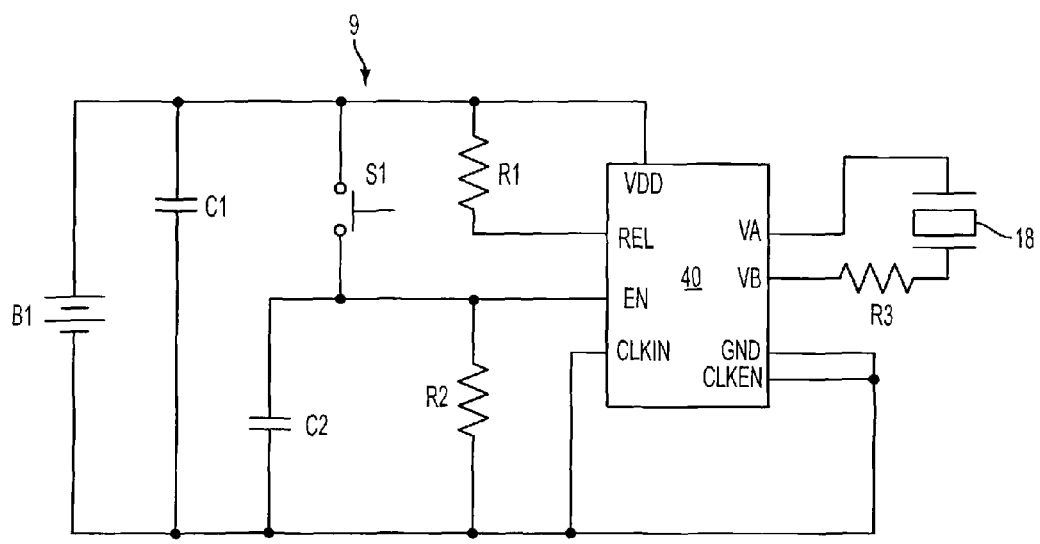
FIG. 4 illustrates a control circuit for operating a pump.

In one construction, as shown in FIG. 4, the micro piezoelectric pump 18 may be driven by a miniature circuit 9 that includes an integrated circuit (IC) driver 40. The miniature circuit 9 may further include, for example, resistors R1 and R2, capacitors C1 and C2, at least one switch S1, and a low voltage direct current (DC) source B1 (such as, a 1.5 volts or 3.0 volts battery) in order to power the driver 40. The driver, 40, such as, a Supertex HV 852 low noise and inductorless driver is a high voltage and low alternating current power source. The driver 40 converts the low voltage DC input from B1 to a high voltage alternating current (AC) output across the pump 18. For example, at 3.0 volts DC input, the driver 40 develops at least 150V peak-to-peak AC voltage, and draws around 23.8 mA 24 mA of current from the battery. At these values, the pumping rate for the micro piezoelectric pump 18 is around 10 µL/second for water at room temperature. The push button switch S1 is the trigger for timer when S1 is closed briefly the pump will run a predetermined time, and shut off itself based on the values of R2 and C2. The miniature circuit 9 can have a very low quiescent supply current of about 1 µA, obviating the need for a separate power switch to control the power when the pump is not in operation.

The circuit including the driver 40 draws a current of about 30 mA when it is running for energy efficient operation. Nevertheless, other values are possible for the current. The circuit can be provided on a conventional circuit board in various sizes. In one construction, the circuit board may measure around 8×13 mm² in size so that it can readily fit into the toothbrush handle 10.

Figure 5:
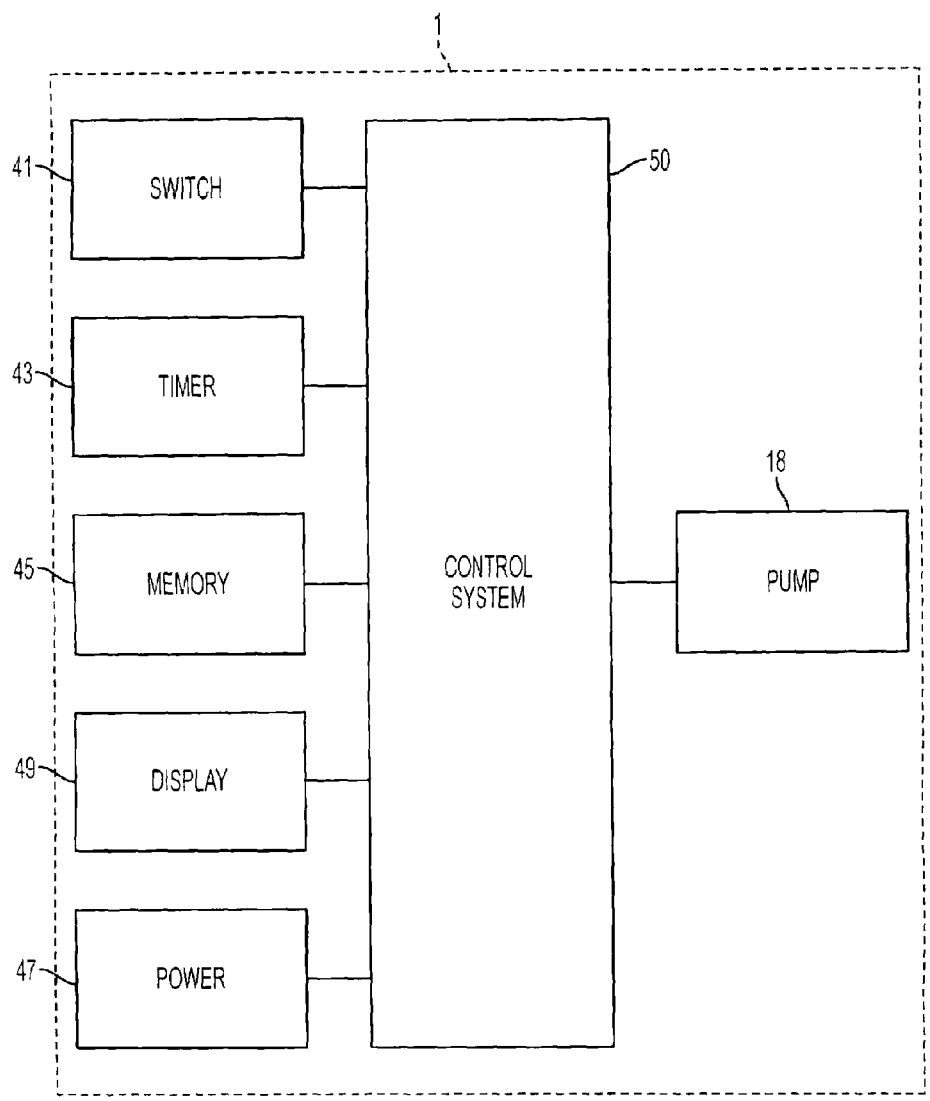
FIG. 5 is a functional block diagram of a control system for operating a pump.

Referring to FIG. 5, a control system 50, as an alternative to or in conjunction with one or more aspects of circuit 9 in FIG. 4, may be used to drive the piezoelectric pump 18 of the toothbrush 1. FIG. 5 illustrates a block diagram for one or more constructions of a control system 50 for driving the pump 18. One or more of the components shown in FIG. 5 may be included within one or more printed circuit boards.

The toothbrush 1 may include a control system 50, a power supply 47 operatively connected to one or more elements of the system 50, and a display 49 operatively connected to one or more components of the system 50. Power supply 47 may include one or more power components, such as a battery or a wired connection to a power source, providing for electrical power to electrical components of the toothbrush 1. The display 49 may display information, such as, switching time (activation or deactivation), pump rate, or other desired information.

In one or more constructions, the control system 50 may include a switch circuitry 41, a timer circuitry 43, and a memory 45. The control system 50 is operatively coupled to memory 45. Memory 45 stores data installed or programmed by the user. Memory 45 may be any programmable type in which nonvolatile storage can be electrically erased and reprogrammed. Possible alternatives include flash memory, flash ROM, RAM with battery backup. It should be understood that data formatted for toothbrush 1 may be downloaded to memory 45 or data may be preloaded in the memory.

Switch circuitry 41 may include hardware, software, computer-readable instructions, or other components to allow for activating or deactivating the operation of the piezoelectric pump 18. The switch circuitry 41 may be configured to perform the functions for processing signal(s) performing computer-readable instructions, and reading from and writing to a memory 45 associated with the toothbrush 1.

Timer circuitry 43 may include hardware, software, computer-readable instructions, or other components to allow for counting up or counting down time and for outputting such information (for example, switching time) in suitable form for use by the display 49. Timer circuitry 43 may include a crystal oscillator for counting seconds, minutes, etc. Timer circuitry 43 may be configured to perform the functions for processing signal(s) performing computer-readable instructions, and reading from and writing to a memory 45 associated with the toothbrush 1 operating in a timer mode.

The control system 50 may activate the pump 18 by a switch, 41 with a timer where the pump is turned OFF (that is, deactivated) automatically after a predetermined time. This activation switch, 41 may be controlled by a button 22 that may be located below the toothbrush neck 11 or elsewhere on the toothbrush 1, such as, between the toothbrush head 12 and handle 10. The duration of time that the pump is turned ON or activated may be adjusted as desired by the user.

Figure 6A:
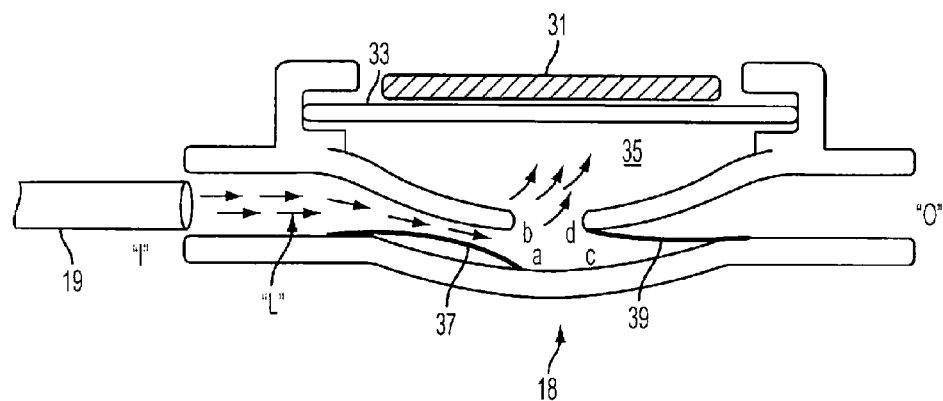
FIGS. 6A and 6B illustrate a representative operation of a piezoelectric pump construction as liquid flows from the pump from the reservoir via a fluid pathway.
Figure 6B:
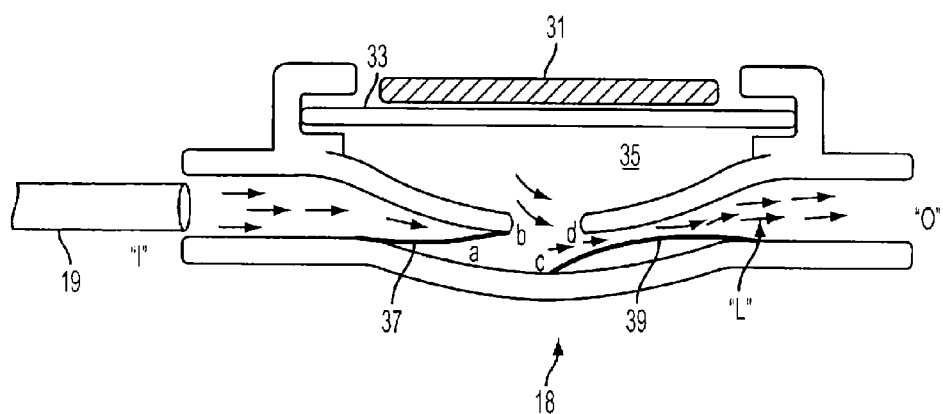
Figure 7:
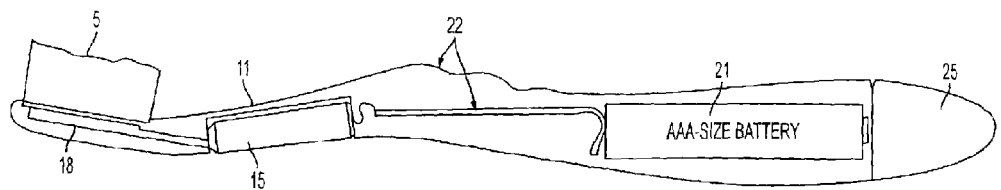
FIG. 7 is a side elevation view of an alternative toothbrush construction having a reservoir disposed in a neck portion.

The operation of the piezoelectric micro pump 18 is illustrated using FIGS. 6A and 6B. The micro pump 18 includes, an actuator 31 fixed on a flexible membrane 33, which is placed on top of the pump chamber 35, and two double valve flaps 37 and 39. The two double valve flaps 35 and 37 act as a control for the liquid, allowing liquid to flow only in one direction, namely towards the outlet 50.

Referring to FIG. 6A, when the double flap valve 37 is open (at position "a") and the double flap valve 37 is closed (at position "d"), liquid L from the flexible tube 19 is allowed to flow into the chamber 35 through the pump's input side I. It is to be understood that the negative pressure in the chamber caused by the upward movement of the membrane enables flow of the liquid. After the chamber 35 fills up to an allowable or determined quantity, the flap 37 closes by moving to position "b" as shown in FIG. 6B, and does not let in more liquid into the chamber 35. It is to be understood that downward movement of the membrane cause a positive pressure in the chamber such that backflow of the liquid is caused against the chamber-side portion of the flap 37. At the same time, the double valve flap valve 39 opens by moving to position "c" to enable the liquid L in the chamber 35 to flow out of the chamber 35 into output O. This output liquid flows through one of the outlets of the toothbrush head portion 12.

In one construction, a kit includes a toothbrush and at least one cartridge containing an active agent. A user may select among multiple cartridges for a desired treatment. If the active agents have different intervals of application, the toothbrush may be provided with a feature, for example, a dial or a slider, to enable the user to select the appropriate setting. Similarly, a single cartridge can come pre-loaded with multiple active agents that may be selectively accessed and delivered by a switch or the like. The kit can also include a dentifrice if desired.

FIGS. 7-11 show a toothbrush construction in which the reservoir 15 is positioned at the bottom of the neck portion 11. A relatively short (e.g., about 10-20 mm) channel connects the reservoir 15 to outlet(s) located in the head portion.

Advantageously, by locating the reservoir 15 in the neck portion 11, the distance that the medium is dispensed to the head is minimized. In this way the implement is less prone to clogging, the required volume of the reservoir 15 may be reduced, or the reservoir 15 may be more easily replaced for changing or replenishment of the active agent.

Figure 8:
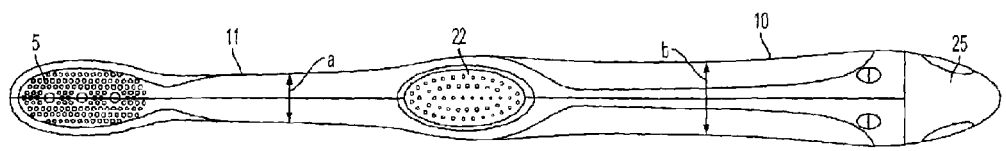
FIG. 8 is a top plan view of the toothbrush of FIG. 7.

With reference to FIG. 8, the cross-sectional area denoted in the "b" dimension of the handle portion 10 may be suitably selected to provide sufficient storage space for the battery 21, such as an AAA type or other generally cylindrical battery, while also providing ergonomic characteristics to permit easy gripping and manipulating of the toothbrush. The neck portion 11 has a cross-sectional area denoted in the "a" dimension which is generally less than that of the handle portion 10 and may be suitably selected to provide sufficient storage space for the reservoir 15. Either or both of the neck portion 11 and handle portion 10 may have contours such that the respective cross sectional area ("a" and/or "b") is non-uniform. Given these considerations, the ratio of the average cross-sectional area of the handle portion "b" to the average cross-sectional area of the neck portion "a" usually satisfies the relationship $1 < b/a \leq 5$, (e.g., the ratio of b over a is greater than one and less than or equal to five) and often $1.2 \leq b/a \leq 4$ (e.g, ratio of b over a is greater than 1.2 and less than or equal to four). Nevertheless, other values of the ratio are possible.

Figure 9:
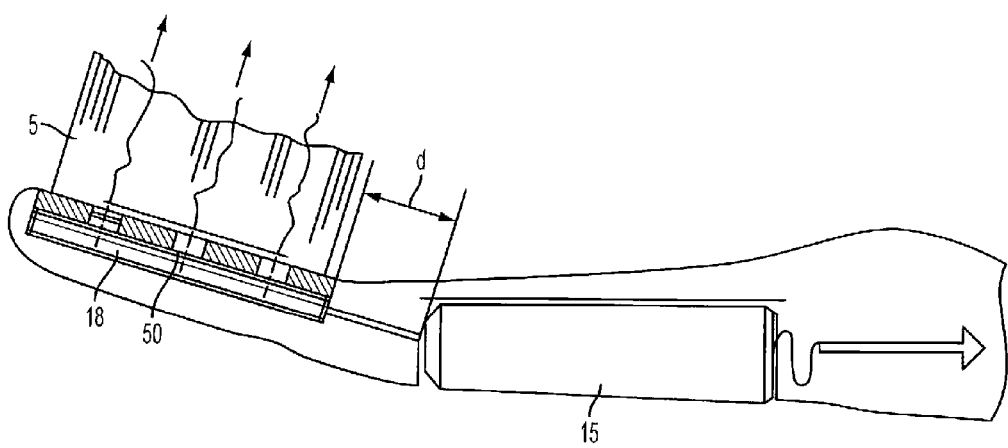
FIG. 9 is a side elevation view of a toothbrush having a piezoelectric pump in the head portion with a reservoir in a neck portion.

Referring to FIG. 9, micro piezoelectric pump 18 is positioned beneath the bristles 5 in the toothbrush head. Upon activation of the switch 22, the pump 18 draws a quantity of the medium from the reservoir 15 through a channel toward the head. The length of the channel (d) may range, for example, from about 10 to 20 mm. The medium is delivered through one or more outlets and through the bristles 5 as indicated by the arrows in FIG. 9.

Figure 10:
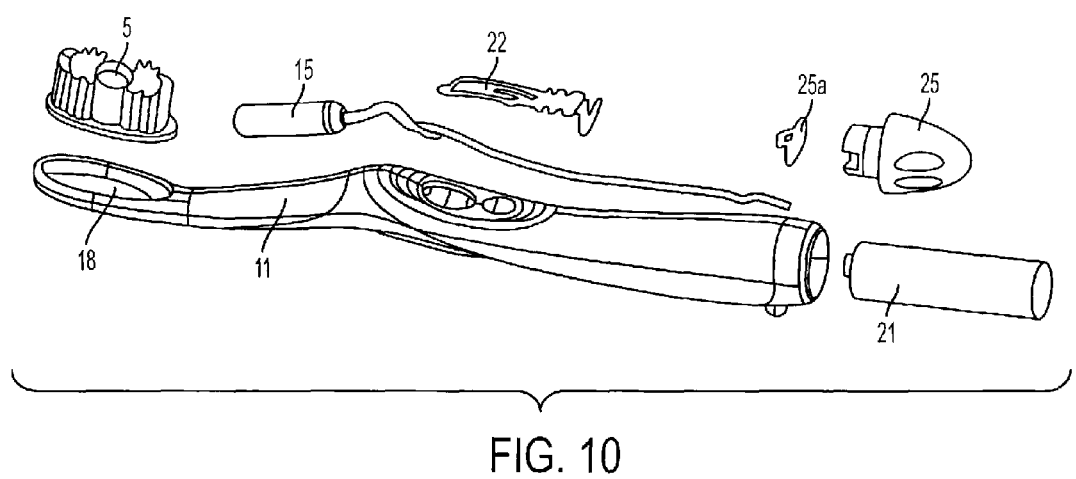
FIG. 10 is an exploded view of the toothbrush of FIG. 7.

FIG. 10 is an exploded view showing the various components of the toothbrush of FIG. 9. A metal battery contact 25a is coupled to the end cap 25 which encloses the battery 21. The neck section 11 houses the reservoir 15.

The toothbrush 1 optionally may be provided with compartments and/or access panels for access to the various components, such as the power source and reservoir. The power source may be, for example, a replaceable or rechargeable battery.

Optionally, a user-activated switch, such as a dial (not shown), can have multiple settings for selecting one of several active agents. For example, the dial can have a first setting for oxidizer/whitener treatment, a second setting for breath freshener treatment, and a third setting for antimicrobial treatment. The dial setting instructs the timing circuit to activate the pump 18 for a time interval appropriate for the selected active agent.

Figure 11:
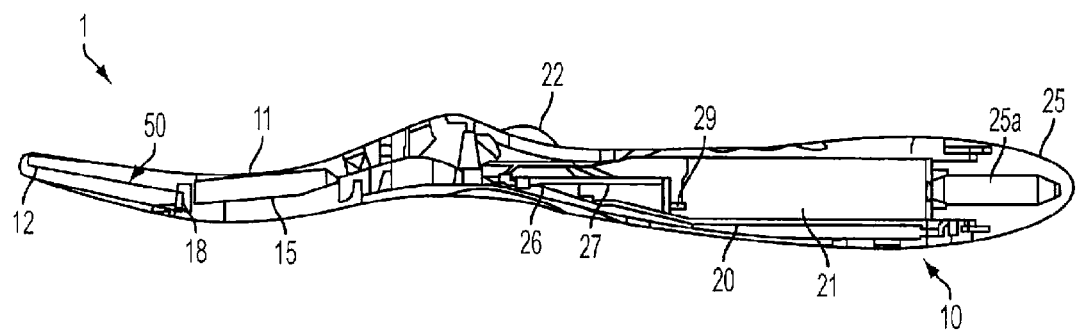
FIG. 11 is a side elevational view of an alternative toothbrush construction with the pump located next to the head and the reservoir in the neck.

As illustrated in FIG. 11, the handle 10 may include a sheath or sleeve 20 which extends in the longitudinal direction of the handle 10 and is made of electrically conductive material. Both the handle 10 and the sleeve 20 are open to the rear, thus forming a cavity which can be closed from the rear by a threaded closure part 25. The battery 21 may be a commercially available, non-rechargeable cylindrical battery, with a defined power, e.g. 1.5 V. Alternatively, a button cell or rechargeable storage battery could be used as a power source.

A spring contact 29 for the positive pole of the battery 21 is fitted in the sleeve 20, on a transverse wall, and is connected to the pump 18 via an electric line 26. The electrical connection can be interrupted by means of the switch 22.

The closure part 25 may be provided with a threaded stub 25a made of an electrically conductive material and can be screwed into the handle 1 and/or into the sleeve 20. The threaded stub 25a may be provided with a contact surface which, with the closure part 25 screwed in, comes into abutment against the negative pole of the battery 21 inserted into the sleeve 20. The negative pole is electrically connected to the drive circuit 18 via the threaded stub 25a, the sleeve 20 itself, and a line 27 which connects the sleeve 20 to the pump 18. Instead of being transmitted via the electrically conductive sleeve 20, it would also be possible for the power from the negative pole to be transmitted in some other way, for example using wires or an electrically conductive plastic.

The toothbrush 1 may be used by applying toothpaste to the bristles and brushing the teeth in a conventional manner. The active agent may be administered by activating the switch, e.g., depressing button 22, to activate the pump 18, which causes the medium containing the active agent to be delivered though the outlet(s). The switch may instruct the timing circuit to activate the pump 18 for a predetermined time, which in turn dispenses the active agent in a predetermined amount. Alternatively, the active agent may be administered in a user-defined amount, for example, dispensation may occur for the duration that the button 22 is depressed. The active agent may then be applied to the teeth using the bristles. The active agent may be administered before, during, or after brushing.

In the toothbrush constructions described herein, the active agent itself may be contained in the reservoir 15. In other words, it is not necessary to generate the active agent internally or in situ. This simplifies the construction of the toothbrush and avoids the need to handle any byproducts associated with the synthesis of the active agent. Alternatively, an agent in one reservoir may be delivered via a delivery device to another reservoir where it is "activated," where it is then delivered via another delivery device to the one or more outlets. A delivery system in the toothbrush constructions may employ multiple connections that are direct or indirect.

Non-limiting examples of active agents which can be used include antibacterial agents, such as chlorhexidine, cetyl pyridinium chloride, triclosan, stannous compounds, herbal extracts and zinc compounds; oxidative or whitening agents, such as hydrogen peroxide, urea peroxide, sodium percarbonate, and PVP-$H_2O_2$; supercharged fluoride delivery ingredients (such as dicalcium phosphate dihydrate and others disclosed in U.S. Pat. No. 5,785,956); tooth sensitivity ingredients, such as $KNO_3$; occluding agents, such as Novamin® bioactive glass, sodium silicate, and arginine salts such as arginine bicarbonate; gum health actives, including those which reduce inflammation pathways and/or interfere in bacterial processes which produce inflammatory stimuli, such as polyphenols (such as baicalin and catechin), herbal extracts and triclosan; nutritional type ingredients, such as vitamins, minerals, amino acids, vitamin E, and folic acid; tartar control or anti-stain ingredients, including phosphate salts, polyvinylphosphonic acid, PVM/MA copolymer; enzymes, such as those used for plaque disruption; sensate ingredients, such as those providing cooling, tingle, or heat sensations; flavors and flavor ingredients; anti-cavity or enamel repair agents; breath freshening ingredients; oral malodor reducing agents; anti-attachment agents, such as ethyl lauroyl arginate and silicone polymers; diagnostic solutions, such as plaque-indicator dyes; colorants or other aesthetic agents; and combinations thereof. Examples of flavors and flavor ingredients include essential oils, menthol, carvone, and anethole, and various flavoring aldehydes, esters, and alcohols. Examples of essential oils include oils of spearmint, peppermint, wintergreen, sassafras, clove, sage, eucalyptus, marjoram, cinnamon, lemon, lime, grapefruit, and orange.

The active agent and/or its medium can be selected to complement a toothpaste formula, such as by coordinating flavors, colors, aesthetics, or active ingredients. A flavor can be administered to create a gradual flavor change during brushing, which presently is not possible using toothpaste alone.

The active agent may be compatible with toothpaste, or may be unstable and/or reactive with typical toothpaste ingredients. Non-limiting examples of components which tend to be unstable and/or reactive with typical toothpaste ingredients include hydrogen peroxide, sodium fluoride, various calcium salts, cetyl pyridinium chloride, ethyl lauroyl arginate, silicone polymers, enzymes, and chlorhexidine. The active agent also may be a tooth cleaning agent to boost the overall efficacy of brushing. Such tooth cleaning agents may or may not be compatible with the toothpaste ingredients.

The active agent can be provided in any suitable vehicle, such as in aqueous solution or in the form of gel or paste. In one example of an implementation, oxygen can aid in oxidation processes such as tooth whitening or air to enhance whole mouth flavor sensation. The use of air can increase the rate of diffusion of the flavor in the mouth. Non-limiting examples of vehicles include water, monohydric alcohols such as ethanol, poly(ethylene oxides) such as polyethylene glycols such as PEG 2M, 5M, 7M, 14M, 23M, 45M, and 90M available from Union Carbide, carboxymethylene polymers such as Carbopol® 934 and 974 available from B.F. Goodrich, and combinations thereof. The selection of a suitable vehicle will be apparent to persons skilled in the art depending on such factors as the properties of the active agent and the desired properties of the medium, such as viscosity.

The quantity of the medium dispensed may vary over a wide range depending on such factors as the identity of the active agent and its concentration in the medium. The quantity usually ranges from about 1 to about 500 µL per use, more usually from about 10 to about 100 µL. For example, the pump 18 may be configured to deliver 10 µL of 20% cetylpyridinium chloride gel over a period of 30 seconds, e.g., for application during the first 30 seconds of brushing the teeth. An advantage of this delivery is that ingredients incompatible with the toothpaste are exposed to the toothpaste as little as possible.

The reservoir 15 may contain a quantity of the active agent medium intended for a single use or a small number of uses, or may facilitate repeated use over an extended period of time, e.g., up to several months or several years (if used with a toothbrush having a replaceable head for example). The size of the reservoir 15 may be selected to be compatible with the desired overall dimensions of the toothbrush 1, particularly the neck portion 11, as well as such factors as the stability of the active agent and the quantity of medium administered during each application.

The supply of active agent in the reservoir 15 may be free or substantially free of components which are incompatible with the active agent and/or the medium containing the active agent, such as incompatible toothpaste components as previously identified. In one aspect, the reservoir 15 may be free or substantially free of toothpaste, as toothpaste is separately applied to the bristles by the user. Alternatively as noted above, an active agent may be originally retained in one reservoir and then transferred to another reservoir where it is activated just prior to delivery, which may be useful in certain conditions or circumstances.

The following examples are provided for illustrative purposes and should be construed as illustrative and not limiting.

EXAMPLE 1

Table I illustrates a cetylpyridinium chloride concentrate that may be dispensed from a toothbrush reservoir during brushing as an antibacterial agent.

TABLE I

| Ingredient | Wt % |
|---|---|
| Carbopol 974P | 1-2 |
| PEG 600 | 10 |
| FD&C blue #1(1% solution in water) | 0.5 |
| Cetylpyridinium chloride | 20 |
| Water | Q.S. |

EXAMPLE 2

Table II shows a hydrogen peroxide solution that may be dispensed from a toothbrush reservoir during brushing as a whitening booster.

TABLE II

| Ingredient | Wt % |
|---|---|
| Carbopol 974P | 1-2 |
| Hydrogen peroxide | 30 |
| Water | Q.S. |

EXAMPLE 3

Table III illustrates a hydrogen peroxide gel that may be dispensed from a toothbrush reservoir during brushing as a whitening liquid. The gel also may be applied post-brushing for tooth whitening.

TABLE III

| Ingredient | Wt % |
|---|---|
| Water | 10.07 |
| Carbopol 974 | 1.00 |
| 95% Ethyl alcohol | 34.8 |
| Glycerin | 5.00 |
| PEG 600 | 10.00 |
| PEG 2M | 14.00 |
| Hydrogen peroxide | 25.00 |
| 85% Phosphoric acid | 0.05 |
| Monobasic sodium phosphate | 0.05 |
| Total | 100.00 |

EXAMPLE 4

Table IV shows a phosphoric acid solution that may be dispensed from a toothbrush reservoir during brushing as a whitening liquid. The solution has a pH of about 4.0.

TABLE IV

| Ingredient | Wt % |
|---|---|
| Purified water | 25.1 |
| Carbopol 974 | 1.00 |
| 95% Ethyl alcohol | 34.8 |
| Glycerin | 5.00 |
| PEG 2M | 15.00 |
| Urea peroxide | 18.00 |
| 85% Phosphoric acid | 0.10 |
| Monobasic sodium phosphate | 1.0 |
| Total | 100.00 |

EXAMPLE 5

Table V illustrates another hydrogen peroxide solution that may be dispensed from a toothbrush reservoir during brushing as a whitening booster. The composition alternatively may be applied to the teeth after brushing as a whitening agent.

TABLE V

| Ingredient | Wt % |
|---|---|
| Carbopol 974P | 1 |
| 95% ethyl alcohol | 34.8 |
| Glycerin | 5 |
| PEG 600 | 10 |
| PEG 2M | 14 |
| 85% phosphoric acid | 0.05 |
| Monobasic sodium phosphate | 0.05 |
| Hydrogen peroxide | 25 |
| Water | Q.S. |

EXAMPLE 6

Alternative liquid whitening gels are prepared by modifying the base formula of Example 5 by adding either (1) 2 to 5 wt % polyethylene (PE) powder having an average particle size of 6 to 8 microns; (2) 1 to 5 wt % polytetrafluoroethylene (PTFE) powder having particle size of 5 to 6 microns; (3) 0.8 to 2.5 wt % polypropylene (PP) powder having a particle size of 4 to 50 microns; (4) 2 to 5 wt % PE powder and 0.11 to 0.4 wt % titanium dioxide powder having a particle size of 10 to 45 microns. Examples of gels having the polymer and/or inorganic titanium powders incorporated in the base formula are shown in Tables VI and VII.

TABLE VI

| | A (wt %) | B (wt %) | C (wt %) | D (wt %) | E (wt %) | F (wt %) | G (wt %) |
|---|---|---|---|---|---|---|---|
| Base Formula | 99.0 | 98.0 | 95.0 | 98.0 | 95.0 | 99.2 | 97.5 |
| +PE | — | — | — | 2.0 | 5.0 | — | — |
| +PTFE | 1.00 | 2.0 | 5.0 | — | — | — | — |
| +PP | — | — | — | — | — | 0.8 | 2.5 |

TABLE VII

| | GA (wt %) | H (wt %) | I (wt %) | J (wt %) | K (wt %) | L (wt %) |
|---|---|---|---|---|---|---|
| Base Formula | 99.5 | 97.90 | 97.80 | 97.60 | 94.90 | 99.5 |
| +PE | — | 2.00 | 2.00 | 2.00 | 5.00 | — |
| +TiO$_2$ | — | 0.10 | 0.20 | 0.40 | 0.10 | 0.5 |
| +TiO$_2$ coated mica | 0.5 | — | — | — | — | — |

EXAMPLE 7

Table VIII shows another exemplary composition of a liquid whitening gel that may be dispensed from a reservoir of a toothbrush during brushing as described herein.

TABLE VIII

| Liquid Gel Formula | Wt % |
|---|---|
| Carbomer | 1.00 |
| PEG 600 | 9.96 |
| BHT | 0.03 |
| Glycerin | 4.98 |
| Water | 17.00 |
| Ethyl alcohol | 34.67 |
| PEG 2M | 13.95 |
| $H_2O_2$ (35%) | 17.93 |
| Sodium Phosphate | 0.05 |
| Phosphoric acid | 0.05 |
| Titanium dioxide | 0.38 |

EXAMPLE 8

Table IX example shows the composition of a breath protection gel that is dispensed from a toothbrush reservoir as described herein.

TABLE IX

| Ingredient | Wt % |
|---|---|
| Carbopol 974P | 1 |
| PVM/MA copolymer | 10 |
| Triclosan | 20 |
| Ethyl alcohol | 40 |
| Zinc gluconate | 20 |
| Water | Q.S. |

What is claimed is:

1. An oral care implement comprising; a head extending along a longitudinal axis and having tooth cleaning elements, a reservoir for storing a liquid, the reservoir being connected to an end of a channel, an outlet disposed in the head, a piezoelectric pump disposed in the head beneath the tooth cleaning elements to deliver the liquid from the reservoir via the outlet, the piezoelectric pump having an input port connected to another end of the channel and an output port joined to the outlet, a transverse plane substantially perpendicular to the longitudinal axis, the transverse plane intersecting the piezoelectric pump and at least one of the tooth cleaning elements, a valve that allows the liquid to flow only toward the outlet, and wherein the reservoir is a collapsible bag or container that ensures that negative pressure does not build up in the reservoir.

2. (Previously Presented The oral care implement of claim 1, further including a handle, a neck and a circuit for operating the piezoelectric pump, wherein the reservoir is disposed in the neck.

3. The oral care implement of claim 1, wherein the reservoir is disposed in a neck of the oral care implement.

4. The oral care implement of claim 1, wherein the reservoir is radially collapsible.

5. The oral care implement of claim 1, wherein the reservoir is longitudinally collapsible.

6. The oral care implement of claim 1, wherein the reservoir prevents generation of air bubbles during the liquid transportation to the outlet.

7. The oral care implement of claim 1, wherein the reservoir contains an active agent.

8. The oral care implement of claim 1, wherein the reservoir contains a plurality of active agents selectively deliverable to the outlet.

9. The oral care implement of claim 1, further comprising a circuit having a self timer so that upon activating the piezoelectric pump, the piezoelectric pump deactivates at a predetermined set time.

10. The oral care implement of claim 1, wherein the outlet comprises a plurality of outlets in the vicinity of the tooth cleaning elements.

11. The oral care implement of claim 1, further comprising an activator to operate the piezoelectric pump, wherein the activator comprises an adjustable switch to select one of a plurality of active agent treatments.

12. The oral care implement of claim 1, wherein the reservoir contains a liquid; and wherein the liquid in the reservoir comprises an active agent selected from the group consisting of antibacterial agents, oxidative or whitening agents; enamel strengthening or repair agents; tooth erosion preventing agents; tooth sensitivity ingredients; gum health actives; nutritional ingredients; tartar control or anti-stain ingredients; enzymes; sensate ingredients; flavors or flavor ingredients breath freshening ingredients; oral malodor reducing agents; anti-attachment agents or sealants; diagnostic solutions; occluding, agents, dry mouth relief ingredients; catalysts to enhance the activity of any of these agents; colorants or aesthetic ingredients; and combinations thereof.

13. The oral care implement of claim 1. wherein the active agent is selected from the group consisting of (i) an antibacterial agent selected from the group consisting of chlorhexidine, cetyl pyridinium chloride, triclosan, stannous compounds, herbal extracts, and zinc compounds; (ii) an oxidizing or whitening agent selected from the group consisting of hydrogen peroxide, urea peroxide, sodium percarbonate, and PVP-$_2$O$_2$; (iii) a gum health active selected from the group consisting of polyphenols, herbal extracts, and triclosan; (iv) a nutritional ingredient selected from the group consisting of vitamins, minerals, amino acids, vitamin E, and folic acid; (v) tartar control or anti-stain agent selected from the group consisting of phosphate salts, polyvinylphosphoric acid, and PVM/MA copolymer; (vi) a flavor or flavor ingredient selected from the group consisting of menthol carvone, anethole, aldehydes, esters, alcohols, and oils of spearmint, peppermint, wintergreen, sassafras, clove, sage, eucalyptus, marjoram, cinnamon, lemon, lime, grapefruit, or orange; (vii) an occluding agent selected from the group consisting of sodium silicate, bioactive glass and arginine salts; (viii) an anti-attachment agent selected from the group consisting of ethyl lauroyl arginate and silicone polymers; and (ix) combinations thereof.

14. The oral care implement of claim 1 wherein the output port of the piezoelectric pump is directly joined to the outlet.

15. The oral care implement of claim 14 wherein the liquid exiting through the output port of the piezoelectric pump flows through the outlet in a linear direction that is substantially normal to a front surface of the head.

* * * * *